(12) United States Patent
Berger et al.

(10) Patent No.: US 8,249,896 B1
(45) Date of Patent: *Aug. 21, 2012

(54) METHOD OR SECURE DIAGNOSTIC SCREENING, SERVICING, TREATMENT, AND COMPLIANCE MONITORING FOR SLEEP APNEA FOR OIL AND GAS OFFSHORE WORKERS, CONSTRUCTION WORKERS AND HEAVY EQUIPMENT WORKERS

(75) Inventors: Mark Berger, Houston, TX (US); Helen Francis Berger, Houston, TX (US)

(73) Assignee: MK3SD, Ltd., Houston, TX (US)

( * ) Notice: Subject to any disclaimer, the term of this patent is extended or adjusted under 35 U.S.C. 154(b) by 605 days.

This patent is subject to a terminal disclaimer.

(21) Appl. No.: 12/509,189

(22) Filed: Jul. 24, 2009

Related U.S. Application Data

(63) Continuation-in-part of application No. 11/679,085, filed on Feb. 26, 2007, now Pat. No. 7,599,892.

(51) Int. Cl.
*G06N 5/00* (2006.01)

(52) U.S. Cl. ................ 705/3; 706/3; 600/300

(58) Field of Classification Search ......... 705/2, 3; 600/300
See application file for complete search history.

(56) References Cited

U.S. PATENT DOCUMENTS

| 6,171,258 | B1 * | 1/2001 | Karakasoglu et al. | 600/529 |
| 6,497,658 | B2 * | 12/2002 | Roizen et al. | 600/301 |
| 6,993,380 | B1 * | 1/2006 | Modarres | 600/544 |
| 7,190,995 | B2 * | 3/2007 | Chervin et al. | 600/544 |
| 7,593,767 | B1 * | 9/2009 | Modarres | 600/544 |

* cited by examiner

*Primary Examiner* — Lena Najarian
*Assistant Examiner* — Teresa Woods
(74) *Attorney, Agent, or Firm* — Buskop Law Group, PC; Wendy Buskop

(57) ABSTRACT

A secure method for delivering sleep apnea diagnostic services on an at least one operator of heavy equipment to a company. The sleep apnea diagnostic services are delivered by a general coordinator. The system includes at least one processor connected to an input device, an output device, and a data storage. The data storage includes a plurality of secure computer instruction. The processor is in encrypted communication with a network which is in encrypted communication with at least one company device.

25 Claims, 12 Drawing Sheets

Health Screening Survey
Step 1 of 3

Company Information

Company: [____100____]   Operator #: [__102__]

Classification: [____104____]   Location: [____106____]

Date of Hire: [_____]  ☐ ☐ YES, I am an applicant!
              108

Personal Information

Last Name: [__110__]   First Name: [__112__]   MI: [114]

DOB: [____116____]   SSN: [____118____]

Sex: [__] 120   Height: [__] 122   Weight: [__] 124 (lbs.)

[Continue to Step 2]

*FIG. 3*

Health screening survey
Step 2 of 3
For each question below, please choose the response that best fits your answer for that Question.

Health information

| Question | Answers | |
|---|---|---|
| 1. Do you have high blood pressure? | ⊙ Yes ⊙ No | 134 |
| 2. Do you have diabetes? | ⊙ Yes ⊙ No | 136 |
| 3. Have you been treated for heartburn? | ⊙ Yes ⊙ No | 138 |
| 4. Do you have heart problems? | ⊙ Yes ⊙ No | 140 |
| 5. Have you ever undergone a heart operation or procedure? | ⊙ Yes ⊙ No | 142 |
| 6. Do you take any of the following medications: isorbide dinitrate, Isordil, Ismo, nitroglycerin, amiadarone or Cardarone? | ⊙ Yes ⊙ No | 144 |
| 7. Do you have sleep apnea? | ⊙ Yes ⊙ No | 146 |
| 8. Do you take any of the following medications: Glucophage, Glucotrol, Actos or Avandia, or any other diabetes medications? | ⊙ Yes ⊙ No | 148 |
| 9. Do you have COPD (emphysema)? | ⊙ Yes ⊙ No | 150 |
| 10. Do you have asthma? | ⊙ Yes ⊙ No | 152 |
| 11. Have you been treated for depression? | ⊙ Yes ⊙ No | 154 |
| 12. Do you snore louder than talking? | ⊙ Yes ⊙ No | 156 |
| 13. Does your snoring bother other people? | ⊙ Yes ⊙ No | 158 |
| 14. Do you take any of the following medications: Plavix, Trental, or Persantine? | ⊙ Yes ⊙ No | 160 |
| 15. Do you take ANY of the following medications: Protonix, Prevacid, Nexium, Pepcid, or Tagamet? | ⊙ Yes ⊙ No | 162 |
| 16. On average, do you urinate more than once per night? | ⊙ Yes ⊙ No | 164 |
| 17. Do you become drowsy while driving? | ⊙ Yes ⊙ No | 166 |
| 18. Does head, back, neck, or joint pain affect your sleeping? | ⊙ Yes ⊙ No | 168 |
| 19. Do you take any of the following medications: Vasotec, Cozar, Lotril, Norvasc, Enalapril, Lisinopril, Hydrolchlothiazide, or Lasix? | ⊙ Yes ⊙ No | 169 |
| 20. Do you take any of the following medications: Inderal, Toprol, Metoprolol, Coreg, or Lopressor? | ⊙ Yes ⊙ No | 170 |
| 21. Do you take any of the following medications: Digoxin, or Coumadin? | ⊙ Yes ⊙ No | 172 |
| 22. Do you sleep restlessly or find the blankets on the floor in the morning? | ⊙ Yes ⊙ No | 174 |
| 23. Has anyone noticed that you quit breathing during your sleep? | ⊙ Yes ⊙ No | 176 |
| 24. Have you awakened from sleep with gasping breaths? | ⊙ Yes ⊙ No | 178 |

Continue to Step 3

FIG. 4

Health Screening Survey
*Step 3 of 3*
Situational Information
Please indicate your chance of dozing under each of the following scenerios

| Situation | Chance of Dozing | | |
|---|---|---|---|
| 1. Sitting and reading | ⊙ Never | ⊙ Slight | ⊙ Moderate | ⊙ High | 
| 2. Watching TV | ⊙ Never | ⊙ Slight | ⊙ Moderate | ⊙ High |
| 3. Sitting inactive in a public place (e.g., a theater or meeting) | ⊙ Never | ⊙ Slight | ⊙ Moderate | ⊙ High |
| 4. As a passenger in a car for an hour without a break | ⊙ Never | ⊙ Slight | ⊙ Moderate | ⊙ High |
| 5. Lying down to rest anytime circumstances permit | ⊙ Never | ⊙ Slight | ⊙ Moderate | ⊙ High |
| 6. Sitting and talking to someone | ⊙ Never | ⊙ Slight | ⊙ Moderate | ⊙ High |
| 7. Sitting quietly after lunch without alcohol | ⊙ Never | ⊙ Slight | ⊙ Moderate | ⊙ High |
| 8. In a truck or car, while stopping for a few minutes in traffic | ⊙ Never | ⊙ Slight | ⊙ Moderate | ⊙ High |

*For Men Only!*
What is your neck size? [ ]

[ Submit Survey ]

*FIG. 5*

Health Screening Survey

*Thank you, USER NAME!*
*We appreciate your taking the time to complete this health screening survey. Your information has been securely processed, and as with all personal medical records, will be kept confidential.*

*FIG. 6*

Example Company Health Screening Survey Rankings

You currently have a total of 86 survey respondents, which have been broken down into six categories based on sex, WA (Witnessed Apnea), and EDS (Excessive Daytime Sleepiness).

Respondents — 198 — 199 — 200

| Sex | WA+ | EDS+ / WA- | EDS- / WA- |
|---|---|---|---|
| Male | 26 | 5 | 44 |
| Female | 2 | 1 | 8 |

There are currently 14 respondents that have been marked for immediate contact due to self-admitted Sleep Apnea. To view a complete list, click here.

To review survey respondents based on more specific criteria, click here for additional reporting tools.

Find a Survey

| SSN: | ☐ ☐ ☐ | Find | — 206 |
| Operator #: | ☐ | Find | — 208 |
| Last Name: | ☐ | Find | — 210 |

Return to Main Menu

*FIG. 7*

Example Company Survey Respondents: Sleep Apnea Alert!

Download Report

| | Name | SSN | Location | Operator # | Sex | WA± | Probability | Alert | Date | Date of Hire | Status |
|---|---|---|---|---|---|---|---|---|---|---|---|
| 1. | Berger, Mark B | 123-45-6711 | Location A | 007 | Male | ⊕ | 1.000 | 🚩 | 3/27/2006 | 3/27/2005 | |
| 2. | berger, mark b | 222-22-222 | Location B | 123 | Male | ⊕ | 1.000 | 🚩 | 2/13/2007 | 2/13/2005 | |
| 3. | Green, Paul | 123-45-6711 | Location B | 00000 | Male | ⊕ | 1.000 | 🚩 | 2/15/2006 | 2/15/2005 | |
| 4. | Michael, Johnson | 999-8897766 | Location A | 000066 | Male | ⊙ | 1.000 | 🚩 | 11/15/2006 | 11/15/2005 | |
| 5. | Smith, James | 123-45-6776 | Location A | abc123 | Male | ⊕ | 1.000 | 🚩 | 11/22/2006 | 11/22/2005 | |
| 6. | Test, Test T. | 111-11-1111 | Location A | 111111 | Male | ⊙ | 1.000 | 🚩 | 2/16/2007 | 2/16/2005 | |
| 7. | O'Grady, John | 123-45-6711 | Location B | 00000 | Male | ⊙ | 0.594 | 🚩 | 2/15/2006 | 2/15/2005 | ✉ |
| 8. | Gordon, John | | Location A | 00000 | Male | ⊕ | 1.000 | 🚩 | 2/15/2006 | 2/15/2005 | |
| 9. | Fills, Christopher | | Location B | 00000 | Male | ⊕ | 0.666 | 🚩 | 2/15/2006 | 2/15/2005 | |
| 10. | Turk, Larry | | Location B | 00000 | Male | ⊕ | 0.985 | 🚩 | 2/15/2006 | 2/15/2005 | ✉ ☺ |
| 11. | Brady, Kim | | Location B | 00000 | Female | ⊙ | 0.000 | 🚩 | 2/15/2006 | 2/15/2005 | ✉ ☺ |

Complete List of Survey Responses (Recorded on 3/27/2006)

Health Information

1. Do you have high blood pressure? — Yes
2. Do you have diabetes? — Yes
3. Have you been treated for heartburn? — Yes
4. Do you have heart problems? — No
5. Have you ever undergone a heart operation or procedure? — No
6. Do you take ANY of the following medications: Isordil, Ismo, nitroglycerin, Cardarone, or Amiodarone? — No
7. Do you have sleep apnea? — Yes
8. Do you take ANY of the following medications: Glucophage, Glucotrol, Actos, or Avandia, or any other diabetes medications? — Yes
9. Do you have COPD (emphysema)? — No
10. Do you have asthma? — No
11. Have you been treated for depression? — Yes
12. Do you snore louder than talking? — No
13. Does your snoring bother other people? — No
14. Do you take ANY of the following medications: Plavix, Trental, or Persantine? — No

Epworth Information

1. Sitting and reading — Never
2. Watching TV — Never
3. Sitting inactive in a public place (e.g., a theater or meeting) — Never
4. As a passenger in a car for an hour without a break — High
5. Lying down to rest anytime circumstances permit — Moderate
6. Sitting and talking to someone — Slight
7. Sitting quietly after lunch without alcohol — Never
8. In a truck or car, while stopping for a few minutes in traffic — Never

Sex-Specific Information

What is your neck size?

*FIG. 9B*

Complete List of Survey Responses (Recorded on 3/27/2006)
*Health Information*

15. Do you take ANY of the following medications: Protonix, Prevacid, Nexium, Pepcid, or Tagamet? — No
16. On average, do you urinate more than once per night? — No
17. Do you become drowsy while driving? — Sometimes
18. Does head, back, neck, or joint pain affect your sleeping? — Yes
19. Do you take ANY of the following medications: Vasotec, Cozar, Lotril, Norvasc, Enalapril, Lisinopril, Hydrochlorthiazide, or Lasix? — Yes
20. Do you take ANY of the following medications: Inderal, Toprol, Metoprolol, Coreg, Lopressor? — No
21. Do you take ANY of the following medications: Digoxin, Coumadin? — Yes
22. Do you sleep restlessly or find the blankets on the floor in the morning? — Yes
23. Has anyone noticed that you quit breathing during your sleep? — No
24. Have you awakened from sleep with gasping breaths? — Yes

Screening History

| Date | BMI | WA ± | Probability | Alert | Status |
|---|---|---|---|---|---|
| 1. 3/27/2006 | 29.7 | ⊕ | 1.000 | 🔔 | |

*FIG. 9C*

Example Company Survey Respondents: *Female / EDS- / WA-*
Filter/Sort Options

Classification: `<All Classifications> ▼`  — 252

Location: `<All Locations> ▼`  — 254

Treatment Facility: `<All Facilities> ▼`  — 256

Sort by: `Risk ▼` `Desc. ▼`   Then by: `Date of Entry ▼` `Desc. ▼`

[Apply Filter]   [Download Report]

26 Result(s) found   `<Previous`   Page 1 of 1

| Name | SSN | Location | Operator # | Sex | WA± | Probability | Alert | Date | Date of Hire | Status |
|---|---|---|---|---|---|---|---|---|---|---|
| 1. Barna, John | | Location A | 00000 | Male | ⊕ | 1.000 | | 3/27/2006 | 3/27/2005 | |
| 2. Berger, Mark B | 123-45-6711 | Location A | 007 | Male | ⊕ | 1.000 | 📜 | 3/27/2006 | 3/27/2005 | |
| 3. berger, mark b | 222-22-222 | Location B | 123 | Male | ⊕ | 1.000 | 📜 | 2/13/2007 | 2/13/2005 | |
| 4. Elk, Christopher | | Location A | 00000 | Male | ⊕ | 1.000 | | 2/15/2006 | 2/15/2005 | |
| 5. Green, Paul | | Location B | 00000 | Male | ⊕ | 1.000 | 📜 | 11/15/2006 | 11/15/2005 | |
| 6. Lincoln, Larry | 666-55-4444 | Location A | 00000 | Male | ⊕ | 1.000 | | 11/22/2006 | 11/22/2005 | |

METHOD OR SECURE DIAGNOSTIC SCREENING, SERVICING, TREATMENT, AND COMPLIANCE MONITORING FOR SLEEP APNEA FOR OIL AND GAS OFFSHORE WORKERS, CONSTRUCTION WORKERS AND HEAVY EQUIPMENT WORKERS

CROSS-REFERENCE TO RELATED APPLICATIONS

The present application is a Continuation-in-Part of U.S. patent application Ser. No. 11/679,085, filed on Feb. 26, 2007; entitled "Method for Secure Diagnostic Screening, Servicing, Treatment and Compliance Monitoring for Sleep Apnea in Truck Drivers", which is incorporated in its entirety by reference.

FIELD

The present embodiments generally relate to a secure method for providing sleep apnea diagnostic services on at least one operator, such as a heavy equipment operator for drill equipment, or an operator in a refinery or petrochemical plant for at least one company.

BACKGROUND

Sleep apnea is very common, particularly in the heavy equipment operator population. Studies show that up to 28 percent of heavy equipment operators may be afflicted. Primary risk factors include being male, overweight, and over the age of forty. Fortunately sleep apnea can be diagnosed and, with treatment, quality of life and health benefits can be realized.

For a company, an employee with sleep apnea can cause accidents on the job. Identification of employees with sleep apnea, promptly treating workers with sleep apnea, such as construction workers, heavy equipment operators, oil field drilling operators, chemical plant operators, offshore drill equipment and work over equipment operators, and earth moving equipment operators if treated for their sleep apnea will cause fewer accidents.

Sleep apnea is defined as the cessation of breathing during sleep. Obstructive sleep apnea (OSA) is the most common form of sleep apnea. OSA occurs when the tissues in the back of the throat repetitively collapse during sleep, producing snoring and complete airway blockage. This blockage creates pauses in breathing that occur repeatedly every night. In severe cases they can occur as frequently as every 30 seconds. Alarmingly, they can last up to a full minute. The condition causes the person to wake up repeatedly, having disturbed sleep, and forms of insomnia.

These repetitive pauses in breathing during sleep are accompanied by a reduction in blood oxygen levels and are followed by an arousal response. This response includes a release of substances into the bloodstream, which promote elevation of blood pressure, inflammation, insulin resistance, and a disruption of the brain wave sleep pattern.

The consequences of untreated sleep apnea include poor quality sleep, excessive daytime fatigue, sleepiness, irritability, hard-to-control high blood pressure, diabetes, heart disease, and stroke. Interestingly, and not coincidentally, many of these same medical conditions account for the majority of health-related expenditures in the heavy equipment operator and chemical plant worker and refinery worker populations. Moreover, untreated sleep apnea may be responsible for job impairment, vehicle crashes, and lost loads when operating dump trucks, earth moving equipment, and cranes.

Traditional methods for diagnosing sleep apnea in heavy equipment operators and refinery and chemical workers are time consuming and often interfere with the ability to perform constructions and operation tasks, which results in the company as well as the operator suffering economic deprivation or being fired.

The recognition of the dangers associated with heavy equipment operators and improper sleep is evident in the numerous regulations developed to ensure that heavy equipment operators receive proper sleep.

There exists a need to efficiently screen for sleep apnea in heavy equipment operators.

There exists a need to efficiently determine whether a heavy equipment operator has sleep apnea.

There exists a need to efficiently treat those with sleep apnea.

There exists a need to efficiently monitor a heavy equipment operator's use of sleep apnea treatment equipment.

The present embodiments meet these needs.

BRIEF DESCRIPTION OF THE DRAWINGS

The detailed description will be better understood in conjunction with the accompanying drawings as follows:

FIG. 3 shows an example sleep apnea diagnostic screening questionnaire requesting company personal information and individual personal information usable with the embodiments of this method.

FIG. 4 shows an example sleep apnea diagnostic screening questionnaire requesting health information usable with the embodiments of this method.

FIG. 5 shows an example sleep apnea diagnostic screening questionnaire requesting situational answers from a situational questionnaire usable with the embodiments of this method.

FIG. 6 shows an example of a thank you screen that is shown after completing the health screening survey usable with the embodiments of this method.

FIG. 7 shows an example screen of survey rankings of how a general coordinator would view a plurality of operators after they had completed the health screening survey usable with the embodiments of this method.

FIG. 8 shows an example of survey rankings usable with the embodiments of this method.

FIGS. 9A, 9B, and 9C show screens of an operator after a general coordinator had selected the operator and the answers to the health screening questions usable with the embodiments of this method.

FIG. 10 shows the ability of a general coordinator to filter between different heavy equipment operators that are in the database usable with the embodiments of this method.

Figure 1:
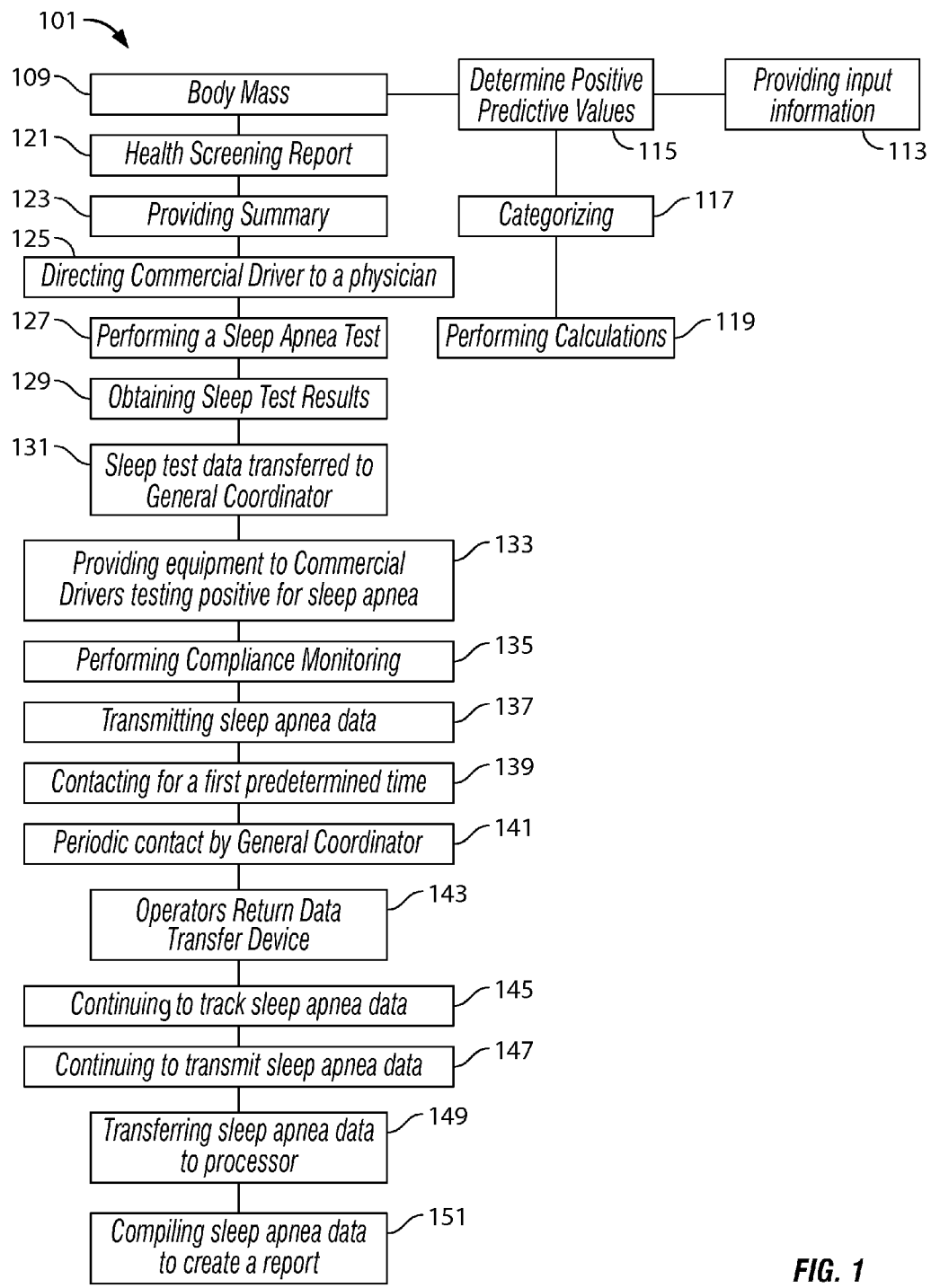
FIG. 1 depicts a general flow diagram of an embodiment of the method.

The present embodiments are detailed below with reference to the listed Figures.

DETAILED DESCRIPTION OF THE EMBODIMENTS

Before explaining the present method in detail, it is to be understood that the method is not limited to the particular embodiments and that they can be practiced or carried out in various ways.

The embodiments relate to a secure method for a general coordinator to deliver to a company sleep apnea screening, sleep apnea treatment, and sleep apnea treatment compliance monitoring on an operator of heavy equipment, refinery equipment, chemical plant equipment, drilling equipment, or similar dangerous large equipment.

The method includes the step of causing an operator to provide input information to a general coordinator. The heavy equipment operator provides input information to the general coordinator by completing a secured sleep apnea diagnostic screening questionnaire.

The secured sleep apnea diagnostic screening questionnaire can request information relating to employee information; the operator's individual personal information, such as his or her age; the operator's personal health information, such as history of high blood pressure; and similar information pertinent to an operator that can be used to screen for sleep apnea.

It can be contemplated that the personal information can include information such as the operator's name, an employee number for each operator, such as 12345; gender for each operator; social security number for each operator, such as 123-45-6078; an alert icon for self admitted sleep apnea; date of input of information; date of hire; or at least one company designated field.

Additionally the secured sleep apnea questionnaire can include a situational questionnaire which can include gender related questions, such as neck circumference, or menopausal status.

In an embodiment of the method, the input information can be provided to the general coordinator by the operator using a company device to provide answers to the sleep apnea screening questionnaire to the general coordinator.

The company device can be in encrypted communication with a network. The network can be in communication with at least one server. The server can be in communication with an input device, an output device, and a data storage.

The data storage can include encrypted computer instruction for the secure sleep apnea screening questionnaire, and encrypted computer instructions for providing a confirmation e-mail to the operator being tested and monitored. The confirmation e-mail can inform the operator of the answers provided to the sleep apnea screening questionnaire, and inform the operator that the information provided in the sleep apnea screening questionnaire is secure and complete.

The e-mail can include an interpretation of the sleep apnea screening questionnaire, such as an individualized health screening report. For example the e-mail is used to inform the operator that he or she is at high risk for sleep apnea and should be tested for sleep apnea.

The general coordinator determines positive predictive values for sleep apnea by categorizing the input information. The general coordinator can use computer instructions stored on a server to perform the task of categorizing the input information.

The input information can be categorized into the following: male Witnessed Apnea Positive (WA+), female Witnessed Apnea Positive (WA+), male Witnessed Apnea Negative (WA−) and Excessive Daytime Sleepiness Positive (EDS+), female Witnessed Apnea Negative (WA−) and Excessive Daytime Sleepiness Positive (EDS+), male Witnessed Apnea Negative (WA−) and Excessive Daytime Sleepiness Negative (EDS−), or female Witnessed Apnea Negative (WA−) and Excessive Daytime Sleepiness Negative (EDS−).

The input information categorized into male WA− and EDS+, require an odds ratio calculation in combination with a liner regression model to determine the predictive value for sleep apnea for each of the heavy equipment operators associated with the input information in the groups male WA− and EDS+, female WA− and EDS+. The input information in the category of male WA− and EDS−, or female WA− and EDS−, and female WA− and EDS+ requires an odds ratio calculation to determine the predictive value of sleep apnea for the operators associated with the input information associated with the input information categorized into the male WA− and EDS−, female WA− and EDS−, and female WA− and EDS+.

The general coordinator can additionally calculate the body mass index for each of the operator and the body mass index can be used in the analysis.

The embodiments of the method can further include the step of the general coordinator providing a health screening service report to the company using the categorized input information. The health screening report is adapted to identify operators with high predictive values for sleep apnea.

The health screening service report can include a rating of individualized numerical scores indicating a positive predictive value, a high, medium, or low positive predictive value. The positive predictive values can be indicated by a red, yellow, or green flag indicating high, intermediate, or low risk for sleep apnea, respectively. It is contemplated that colors alone can be used without any specific icon to indicate high, medium, or low positive predictive values. It is also contemplated that textual words, high, medium, and low can be used in association with each tested operators to indicate high, medium, or low positive predictive values.

The health screening service report can include the company name; the gender of the operator; the presence or absence of sleep apnea; the operator's body mass index, the neck size range of the operator.

It can further be contemplated that the health screening service report in an embodiment includes indicators that the operator has self-admitted hypertension, diabetes, heart disease, lung disease, asthma, heart burn, or frequent urination at night all information usable to determine likelihood of sleep apnea.

Further, the health screening service report can include a look-up table for operator. The look-up tab can be organized according to each operator's employee number, or social security number.

The operators with high predictive values for sleep apnea are directed to go to a physician to obtain a prescription for a sleep apnea sleep test.

A sleep apnea sleep test can be performed on the operators with the high predictive values for sleep apnea. The sleep apnea sleep test can be used to obtain sleep apnea sleep test data.

The sleep apnea sleep test data is transmitted to the general coordinator. The sleep apnea sleep test data is analyzed to determine which of the operators have sleep apnea. The transmission from the physician can be by e-mail, fax, post, or courier.

The general coordinator can provide sleep apnea treatment equipment to the operators with sleep apnea simultaneously with the conclusion of the sleep apnea sleep test.

Providing the sleep apnea treatment equipment to the operators simultaneously with the conclusion of the sleep apnea sleep test is an improvement over traditional methods for treating sleep apnea. With traditional methods for treating sleep apnea it can take several days or weeks for the operator to receive treatment equipment.

The delay in the operator receiving the sleep apnea treatment equipment can delay the operator's hours of work. The delay in returning to work can be a significant cost to the company.

The cost associated with the delays in returning to work has traditionally prevented companies from seeking sleep apnea treatment for operators. By simultaneously providing the sleep apnea treatment equipment to the operators with sleep apnea at the conclusion of the sleep apnea sleep test the delay in the operator's return to work is eliminated.

The sleep apnea treatment continuous positive airway pressure (CPAP) machine has a compliance chip for monitoring the usage and efficacy of the sleep apnea treatment equipment. A data transfer device can be paired with the CPAP machine.

The method includes the step of the general coordinator performing compliance monitoring on the operators that tested positive for sleep apnea. The operators with sleep apnea use the data transfer device to transmit sleep apnea treatment equipment data from the sleep apnea treatment equipment, such as the CPAP machine, to the general coordinator. The sleep apnea treatment equipment data can include data, such as mask leakage, hours of use, and an apnea index based on throat closure during CPAP machine treatment.

The data transfer device is for use with a data transfer system, such as a beeper data transfer system, a cell phone data transfer system, a hardwired system, or a wireless data transfer system. The data transfer system transmits sleep apnea treatment equipment data from the data transfer device to the general coordinator.

An embodiment of the method includes the step of the general coordinator contacting each operator with sleep apnea after a first predetermined period of continuous compliance monitoring.

During the contacting in the first predetermined period, the general coordinator ascertains sleep apnea treatment equipment performance. The general coordinator at this time can conduct trouble shooting to make sure that there is optimal performance of the CPAP machine, and the other sleep apnea treatment equipment. The first predetermined time of compliance monitoring can be between about 2 days to about 3 days. It may be between about 2 weeks to about 4 weeks.

During contacting, the general coordinator can ask the operator if the mask is fitting fine and/or if the mask is leaking If the operator indicates that the mask is leaking the general coordinator can recommended various actions that can remedy the leaking mask, such as tightening the mask, loosening the mask, adjusting the position of the mask and/or connecting hose, or suggesting a different type of mask.

The general coordinator contacts each operator periodically following the first predetermined period of continuous compliance monitoring. The second predetermined period of time can be between about 2 to about 4 weeks. The general coordinator can contact the operators with sleep apnea weekly.

After the second predetermined time the operators with sleep apnea each return the data transfer devices to the general coordinator. The second predetermined time of continuous compliance monitoring can be for a period of time ranging between about 2 weeks to about 6 weeks It can be contemplated that the general coordinator can continue to track sleep apnea treatment equipment data for each heavy equipment operator, by using the compliance chip installed in the CPAP machine past the second predetermined period of time if agreed to by the operator. The general coordinator must comply with specified requirements established by the company and HIPPA requirements regarding privacy.

The next step in this embodiment of the method includes the general coordinator continuing to track sleep apnea treatment equipment data for each operator with sleep apnea.

Each operator with sleep apnea can download their sleep apnea treatment equipment data to an encrypted removable data storage device.

After the operators with sleep apnea download the sleep apnea treatment equipment data, the general coordinator transfers the sleep apnea treatment equipment data from the encrypted removable data storage device to a processor. The transferred sleep apnea treatment equipment data from the encrypted removable data storage device to processor includes between 2 weeks to 4 months of sleep apnea treatment equipment data.

It can be contemplated that the encrypted removable data storage device can be flash memory cards, flash drives, portable hard drives, memory cards, modems, and direct cable connections to the processor, such as a data card from ResMed™ or a removable data storage device from Respironics™

The general coordinator can compile the sleep apnea treatment equipment data using the processor.

The general coordinator can generate a sleep apnea treatment compliance status report. The general coordinator can provide the compliance status report for each of the operators to the appropriate companies.

It can further be contemplated that the method can include delivering sleep apnea screening, sleep apnea treatment, and sleep apnea treatment compliance monitoring simultaneously on a plurality of operators simultaneously to a plurality of companies.

The method can further include providing separate heavy equipment operators results to the companies employing each of the operators simultaneously.

The present method can screen for sleep apnea, treat sleep apnea, and perform compliance monitoring, thus contributing to a reduced risk for potentially dangerous accidents, lost time at work using traditional screening methods, and generally preventing costly loss or damage of equipment, loss of time, preventing injury, and saving lives.

Treated sleep apnea has also been shown to improve an individual's health through better control of blood pressure and diabetes, and a reduced risk for heart attacks and stroke.

It can be contemplated that the method can also include creating additional reports. The additional reports can be reports on the sleep test data, or can be a report on receipts verifying delivery of equipment.

An alternative embodiment of the method can further include the step of confirming the company has a United States Health Insurance Portability and Accountability Act (HIPAA) of 2002, 42 C.F.R. §164, pages 685-740 compliant release for each heavy equipment operator. It is contemplated that the present method can be compliant under the United States Health Insurance Portability and Accountability Act (HIPAA) of 1996, the final regulation of the HIPAA privacy rule of December 2000, and the Final Rule modifications of August 2002.

It can be contemplated that any protected health information (PHI) obtained using the present method can be de-identified when stored and processed to further comply with the requirements of HIPAA.

FIG. 1 is a flow diagram for an embodiment of the method for delivering sleep apnea screening, sleep apnea treatment, and sleep apnea treatment compliance monitoring on a plurality of operators of heavy equipment of a company by a general coordinator 101.

The company can be a commercial earth moving company for building roads.

The general coordinator can be a doctor, health clinic, healthcare network, or a provider of sleep apnea-related services who coordinates with the physician and a third party vendor, such as a manufacturer of CPAP machine and related equipment supplying sleep apnea treatment equipment.

The first step in the method involves the heavy equipment operator providing input information to the general coordinator using a sleep apnea diagnostic screening questionnaire 113. For example, the heavy equipment operator can go to the company's office and complete the sleep apnea diagnostic screening questionnaire by hand.

Figure 2:
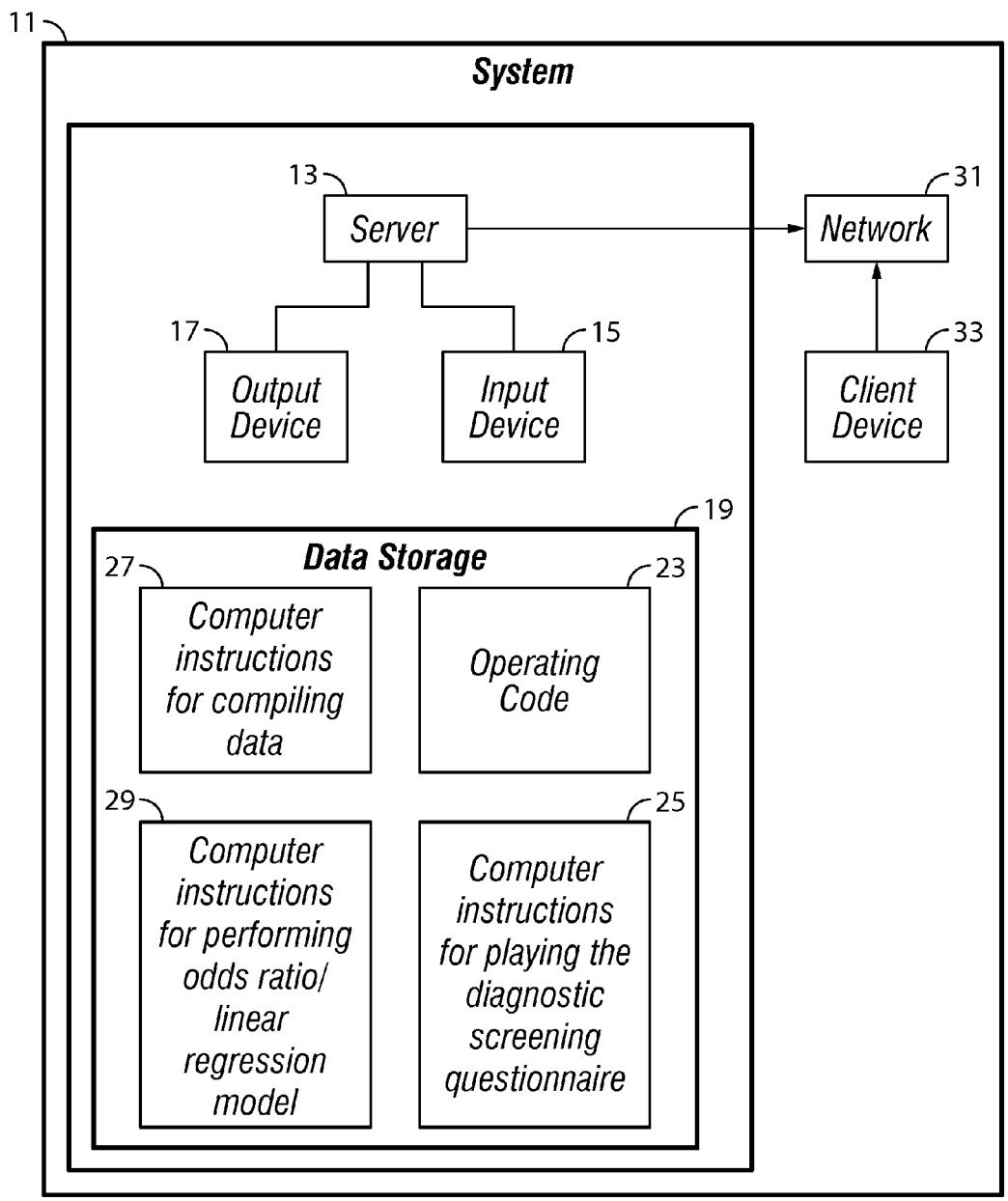
FIG. 2 depicts a system usable with the embodiments of the method.

Alternatively, the general coordinator can use a system such as the one depicted in FIG. 2, which would allow the heavy equipment operator to electronically fill out the sleep apnea diagnostic screening questionnaire using a network, such as the internet, a wide area network (WAN) line, a local area network, and similar communication networks. The network is in communication with a company device, such as a personal computer.

After the sleep apnea diagnostic screening questionnaire is completed the general coordinator determines positive predictive values for sleep apnea for each heavy equipment operator of the company and generates a probability for sleep apnea 115 by categorizing the input information 117 and performing associated calculations 119. The input information is categorized using secured input instructions on a server. The input information can be categorized into the following: male Witnessed Apnea Positive (WA+), female Witnessed Apnea Positive (WA+), male Witnessed Apnea Negative (WA−) and Excessive Daytime Sleepiness Positive (EDS+), female Witnessed Apnea Negative (WA−) and Excessive Daytime Sleepiness Positive (EDS+), male Witnessed Apnea Negative (WA−) and Excessive Daytime Sleepiness Negative (EDS−), or female Witnessed Apnea Negative (WA−) and Excessive Daytime Sleepiness Negative (EDS−).

The input information categorized into male WA− and EDS+, requires an odds ratio calculation in combination with a liner regression model to determine the positive predictive value for sleep apnea for each of the heavy equipment operators associated with the input information in the groups male WA− and EDS+.

The input information in the category of male WA− and EDS−, female WA− and EDS−, and female WA− and EDS+ requires an odds ratio calculation to determine the positive predictive value of sleep apnea for the heavy equipment operators associated with the input information associated with the input information categorized into the male WA− and EDS−, female WA− and EDS, and female WA− and EDS+.

The general coordinator can also make a calculation of the body mass index for each of the operators 109, this is usually done simultaneously when the general coordinator determines the heavy equipment operators probability for sleep apnea 115.

The next step is providing a health screening service report 121. The general coordinator provides the health screening service report to the company that employs the heavy equipment operator.

The health screening service report identifies heavy equipment operators with high predictive values for sleep apnea.

In this embodiment of the method, the general coordinator provides a summary of all positive predictive values using input information to the company 123, such as a listing of the probabilities of sleep apnea.

For example, the health screening service report can indicate that a heavy equipment operator has input data into the sleep apnea diagnostic screening questionnaire that indicates a high likelihood of sleep apnea. The report can then recommend that the heavy equipment operator receive a sleep apnea sleep test.

In an alternative example, the health screening report could indicate that the data input to the sleep apnea diagnostic screening questionnaire indicates that the heavy equipment operator has a low predictive value for sleep apnea and that he does not need to receive a sleep apnea sleep test.

In an embodiment, the heavy equipment operators with high predictive values for sleep apnea are directed to a physician to obtain a prescription for a sleep apnea sleep test 125. Once the heavy equipment operators with sleep apnea receive the prescription for the sleep apnea sleep test the next step is performing a sleep apnea sleep test on the heavy equipment operators with a high positive predictive value for sleep apnea 127, such as an 80 percent to 90 percent positive predictive value.

The sleep apnea sleep test can be performed for one night to obtain sleep apnea sleep test data 129. Typical data can include the amount of time asleep, EEG stages of sleep, the number of respiratory events while asleep, blood oxygen levels while asleep, and leg movements present while asleep.

The next step involves the physician transmitting the sleep apnea sleep test data to the general coordinator 131.

The transmission of the sleep test data can be by electronic transfer, written transmission, or verbal transmission by using traditional means of communication, such as fax, e-mail, or a telephone. The sleep apnea sleep test can be conducted at a free-standing sleep diagnostic facility, a hospital-based sleep diagnostic facility, or an un-attended home using a sleep diagnostic protocol.

After the sleep apnea sleep test, the general coordinator provides sleep apnea treatment equipment to the heavy equipment operators that test positive for sleep apnea 133.

The sleep apnea treatment equipment has a data transfer device paired with the CPAP machine and related equipment, such as masks. The CPAP machine has a compliance chip resident in the CPAP machine to monitor hours of usage, mask leakage, and apnea index. The sleep apnea treatment equipment is supplied simultaneously with the conclusion of the sleep apnea sleep test.

Subsequent to providing sleep apnea treatment equipment to the heavy equipment operators having sleep apnea the general coordinator performs compliance monitoring on the heavy equipment operators that have sleep apnea 135. A receipt can be scanned and uploaded into the files of the operator and provided to the operator's company for the equipment provided to the heavy equipment operator Next, the heavy equipment operator transmits sleep apnea treatment equipment data, such as the CPAP machine's performance and hours of use, from the sleep apnea treatment equipment to the general coordinator 137. The heavy equipment operators initially utilize wireless transmission technology to transmit sleep apnea treatment equipment data to the general coordinator. The wireless transmission of data from the compliance chip to the coordinator can be using a beeper data transfer system, a cell phone data transfer system, or a satellite wireless data transfer system.

The general coordinator then contacts each heavy equipment operator with sleep apnea for a first predetermined period of continuous compliance monitoring 139, such as within the first 72 hours of treatment initiation, to additionally evaluate sleep apnea treatment equipment performance and driver CPAP machine comfort and compliance. Sleep apnea treatment equipment performance can include number of hours and days of usage of the CPAP machine, mask leak quantification, and apnea index, which is the number of times the heavy equipment operator's throat closes off during CPAP machine treatment.

Following the first predetermined period, the general coordinator periodically contacts each heavy equipment operator 141. For example, the general coordinator can periodically contact the heavy equipment operators with sleep apnea for about two to about eight weeks by phone to ascertain sleep apnea treatment equipment performance and the heavy equipment operator's CPAP machine comfort and compliance after the first 72 hours. The periodic contacting could be by the general coordinator or a designate of the general coordinator, such as once a week. The periodic contacting can take place during a second predetermined time of continuous compliance monitoring which may be longer or shorter than the first predetermined time of continuous compliance monitoring.

After the second predetermined time of continuous compliance monitoring, such as between about 15 to about 60 days, each of the heavy equipment operators with sleep apnea perform the step of returning the data transfer device to the general coordinator 143.

If the equipment is not returned, the general coordinator or a designate of the general coordinator continuing to track sleep apnea treatment equipment data for each of the heavy equipment operators with sleep apnea 145. The general coordinator or designate can continue to track sleep apnea treatment equipment data for each of the heavy equipment operators with sleep apnea by requesting the operator to download the CPAP machine's compliance chip data onto a portable memory card.

The heavy equipment operators with sleep apnea perform the step of downloading sleep apnea treatment equipment data to an encrypted removable data storage device 147. The encrypted removable data storage device can be a data card or other flash memory device.

Next the general coordinator or a designee of the general coordinator performs the step of transferring sleep apnea treatment equipment data from the encrypted removable data storage device to a processor 149. The processor can be a personal computer, a wearable computer, a hand-held computer, a lap top computer, or a similar device, such as a cellular telephone with advanced memory capability.

The general coordinator then performs the step of compiling and processing the sleep apnea treatment equipment data using the processor to create a compliance report The compliance report can include information such as average number of hours per night the operator used his or her CPAP machine.

FIG. 2 is an embodiment of the system 11 that can be used with embodiments of the method for a heavy equipment operator to input data into a sleep apnea screening questionnaire. The system 11 includes a server 13, such as a processor associated with data storage having an input device and an output device with the computer instructions resident in the data storage. The server 13 is depicted connected to an input device 15, which can be a keyboard, a tactile display screen, an audio input device with voice recognition software, a cellular device, or similar devices.

The server 13 is also connected to an output device 17, such as a microphone using text to speech software, a digital monitor, a cellular telephone, a printer, a computer, or combinations thereof.

The server 13 is connected to a data storage 19, such as a memory card, a flash drive, or a similar memory device. The data storage 19 contains a plurality of secure computer instructions. For example, the data storage has operating code 23, computer instructions for the sleep apnea diagnostic screening questionnaire 25, computer instructions for performing an odds ratio and/or a linear regression model 29, and computer instructions for compiling data 27.

The server 13 is in encrypted communication with a network 31, such as the internet, a local area network, a wide area network, a virtual private network, a cellular network, a fiber optic network, or other similar networks. The network 31 is in encrypted communication with at least one company device 33, such as a personal computer.

In an embodiment, the computer instructions can further include a dataset using outcomes from at least 500 heavy equipment operators. The dataset can be used to form a useable linear regression model for determining positive predictive values for sleep apnea.

For example, an odds ratio model can be first utilized in determining risk stratification for sleep apnea in all groups or employees of interest in the company. Individual odds ratios can be assigned to specific health conditions and specific symptoms based on results from published medical research. These odds ratios can be modified based on outcome data available on a defined group of heavy equipment operators tested for sleep apnea. A composite odds ratio value can be calculated as the product of all individual odds ratios.

Retrospective analysis of a group of heavy equipment operators tested for sleep apnea demonstrates that a composite odds ratio of 8.0 or greater can be used with male data and, and 1.9 or greater can be used for female data. Witnessed Apnea Negative (WA) and Excessive Daytime Sleepiness Negative (EDS−) would generate a high positive predictive value of at least 85 percent.

A subsequent analysis of over 500 additional heavy equipment operators tested for sleep apnea confirmed an 88 percent positive predictive value for these groups from the odds ratio model.

A retrospective analysis of 100 heavy equipment operators tested for sleep apnea demonstrated that the presence of witnessed apnea (WA+) was highly predictive for sleep apnea. For this reason, all heavy equipment operators reporting witnessed apnea were considered at high risk for sleep apnea. A subsequent analysis of over an additional 500 heavy equipment operators tested for sleep apnea confirmed a 90 percent positive predictive value for this single risk factor.

Subsequent analysis of over 500 more heavy equipment operators confirmed the aforementioned statistical model capable of a greater than 85 percent positive predictive value for sleep apnea in all groups except for male Excessive Daytime Sleepiness Positive (+), Witnessed Apnea (−). For this group it was necessary to apply a linear regression following a composite odds ratio calculation.

To generate the linear regression model for all male heavy equipment operators indicating a positive response for excessive daytime sleepiness EDS (+), witnessed apnea negative WA (−), a model was created by exploring all possible models with main effects and pair-wise interactions with the following variables: body mass index, age, hypertension, diabetes, heartburn, heart condition, snoring, asthma, depression, frequent urination at night, and painful sleep.

The "best" model was chosen by using both forward and backward selection using the AIC criterion (the function step in R). After selecting this model, subjects were assigned a probability of apnea (inverse log odds of linear combination). Using the usual 0.5 cutoff on the estimated probability, a cross-validated positive-predictive value of 0.876 was achieved. To get to the goal of 0.88, a cutoff of 0.65 was preferred. This gave an estimated 0.891 percent positive predictive value using cross-validation.

FIG. 3 shows an exemplary health screening survey requesting company personal information and individual personal information. Company information that a heavy equipment operator may input include name of a company 100, such as Precision Pulmonary Diagnostics, operator number 102, such as 12468, classification 104, such as temporary driver, location 106, such as Houston, Tex., and date of hire 108, such as Feb. 13, 2007.

Personal information that a heavy equipment operator may input includes last name 110, first name 112, middle initial 114, date of birth 116, social security number 118, gender 120, height 122, and weight 124. Other information that is not depicted but can be entered can include an indication of the heavy equipment operator's smoking history, or a history of nasal conditions or sinus conditions, or indications of other health conditions, such as hypertension or diabetes.

FIG. 4 depicts an exemplary sleep apnea diagnostic questionnaire requesting health information such as health conditions, personal symptoms, prior operations, and medications. Some of these questions can include: Do you have high blood pressure? 134, Do you have diabetes? 136, Have you been treated for heartburn? 138, Do you have heart problems? 140, Have you ever undergone a heart operation or procedure? 142, Do you take any of the following medications: isorbide dinitrate, such as Isordil™ or Ismo™, nitroglycerin, amiodarone, such as Cardarone™? 144, Do you have sleep apnea? 146, Do you take any of the following medications: metformin, such as Glucophage™, glyburide, such as Glucotrol™, Actos™, or Avandia™, or any other diabetes medications? 148, Do you have COPD (emphysema)? 150, Do you have asthma? 152, Have you been treated for depression? 154, Do you snore louder than talking'? 156, Does your snoring bother other people? 158, Do you take any of the following medications: Plavix™, Trental™, or Persantine™? 160, Do you take any of the following medications: Protonix™, Prevacid™, Nexium™, Pepcid™, or Tagamet™? 162, On average, do you urinate more than once per night? 164, Do you become drowsy while driving? 166, Does head, back, neck, or joint pain affect your sleeping? 168, Do you take any of the following medications: enalapril, such as Vasotec™, Cozar™, Lotril™, Norvasc™, lisinopril, hydrochlorthiazide, or furosemide, such as Lasix™? 169, Do you take any of the following medications: Inderal™, Toprol™, Metoprolol™, Coreg™, or Lopressor™? 170, Do you take ANY of the following medications: Digoxin™, Coumadin™? 172, Do you sleep restlessly or find the blankets on the floor in the morning? 174, Has anyone noticed that you quit breathing during your sleep? 176, and Have you awakened from sleep with gasping breaths? 178.

FIG. 5 shows an example health screening survey requesting situational answers from a situational questionnaire. The questions ask a heavy equipment operator to input their chance of dozing while performing certain tasks. Typical tasks that are asked include: Sitting and reading 180, Watching TV 182, Sitting inactive in a public place 184, Sitting as a passenger in a car for an hour without a break 186, Lying down to rest anytime circumstances permit 188, Sitting and talking to someone 190, Sitting quietly after lunch without alcohol 192, and Sitting in a truck or car, while stopping for a few minutes in traffic 194. FIG. 4 can also include a question requesting a male heavy equipment operator to input his neck size 195.

FIG. 6 shows an example of a thank you screen that is shown after completing the health screening survey 196. A heavy equipment operator would not be sent to this screen if any of the previous questions asked by the web based questionnaire were not answered.

In an embodiment, the screen depicted in FIG. 5 can also include an electronic copy of a heavy equipment operator's responses to the web based questionnaire for the heavy equipment operator's records. It can also be contemplated that an acknowledgement or verification, such as an e-mail, could also be sent and could include this information.

FIG. 7 shows an exemplary screen of survey rankings of how a general coordinator would view heavy equipment operators after they had completed the sleep apnea diagnostic screening questionnaire. Respondents are split between male and female respondents. In addition, respondents are separated into three different categories based upon the presence or absence of witnessed apneas and the presence or absence of excessive daytime sleepiness determined by each heavy equipment operator's input information and questionnaire responses. The three categories are witnessed apnea positive (WA+) 198, witnessed apnea negative 199 and excessive daytime sleepiness positive (WA-/EDS+), and witnessed apnea negative and excessive daytime sleepiness negative (WA-/EDS-) 200. The witnessed apnea positive 198, the witnessed apnea negative and excessive daytime sleepiness positive 199, and witnessed apnea negative and excessive daytime sleepiness negative 200 categories list the number of male and female heavy equipment operators which relate to each category. Individual heavy equipment operators can be located as well by their social security number 206, operator number 208, and last name 210.

FIG. 8 shows an example of survey rankings for a general coordinator that would be able to select heavy equipment operators and view their status of whether or not they had been contacted and other pertinent information. Heavy equipment operators are listed with information showing their name 212, social security number 214, location 216, operator number 218, gender 220, presence or absence of witnessed apnea 225, risk rating for sleep apnea 224, whether or not they have responded positively to a question asking whether they have sleep apnea, notated as alert 226, date of entry 228, date of hire 229, and status of contacting, scheduling, and testing of the heavy equipment operator 230. The status of contacting the heavy equipment operator 230 can be displayed including an indication that the heavy equipment operator has been referred for testing 231, an indication that the heavy equipment operator has been contacted 233, an indication that the heavy equipment operator has been scheduled for a sleep study 235, and an indication that the heavy equipment operator has completed a sleep study 237. Additional ways that heavy equipment operators can be listed can include additional fields and columns tailored to the needs of a company.

Figure 9A:
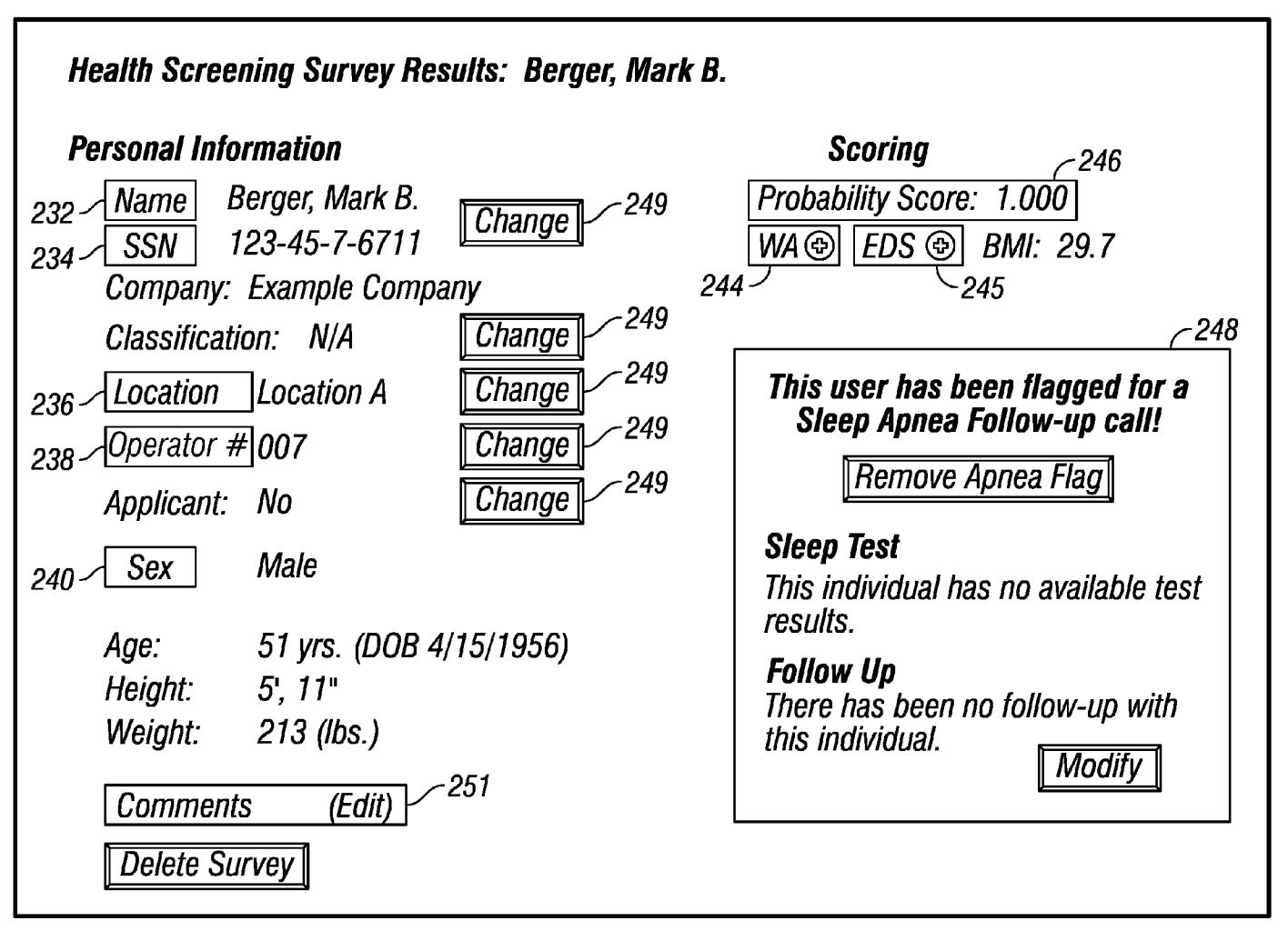

FIG. 9A shows a screen of a heavy equipment operator after a general coordinator selected the operator and the corresponding answers to the health screening questions.

Individual information of the heavy equipment operator is shown including the name 232, social security number 234, location 236, operator number 238, gender 240, presence or absence of witnessed apnea 244, presence or absence of excessive daytime sleepiness 245, probability for sleep apnea 246, whether or not they have been flagged for a sleep apnea follow-up 248, and a comments section 251. Information which can also be shown includes a complete list of the operator's survey responses 250, as shown in FIG. 9B.

FIG. 9A includes change buttons 249, which allow a company or general coordinator to change or correct personal and company information, such as when a heavy equipment operator makes a typographical error. The comments section 251 allows a general coordinator to enter comments regarding a specific heavy equipment operator or specific heavy equipment operator information, such as how a heavy equipment operator was referred, pertinent information regarding a heavy equipment operator's medical history, and other information. FIG. 9C also depicts a screening history 253 for the heavy equipment operator.

FIG. 10 shows that a general coordinator can sort and filter different heavy equipment operators that are in the database in the data storage associated with the processor.

Different filters usable by a general coordinator include classifications 252, locations 254, and treatment facilities 256, which can be a testing facility where a sleep test is performed.

A general coordinator can use one or more sort menus 258, and sort by categories such as probability and status.

Additional filters or sort menus that can be used include a filter or sort menu relating to administrative status, a filter relating to whether an operator is experienced, or a filter relating to date of entry or date of hire.

While these embodiments have been described with emphasis on the embodiments, it should be understood that within the scope of the appended claims, the embodiments might be practiced other than as specifically described herein.

What is claimed is:

1. A method for delivering sleep apnea screening, sleep apnea treatment, and sleep apnea treatment compliance monitoring on a plurality of operators of heavy equipment of a company by a general coordinator comprising:
   a. the sleep apnea screening comprising:
      i. providing input information to the general coordinator using a secured sleep apnea diagnostic screening questionnaire completed by the operator;
      ii. determining positive predictive values for sleep apnea by categorizing input information using computer instructions on a server to categorize the input information into a member of the group consisting of: male Witnessed Apnea Positive (WA+), female Witnessed Apnea Positive (WA+), male Witnessed Apnea Negative (WA−) and Excessive Daytime Sleepiness Positive (EDS+) requiring an odds ratio calculation, female Witnessed Apnea Negative (WA−) and Excessive Daytime Sleepiness Positive (EDS+) requiring an odds ratio calculation, male Witnessed Apnea Negative (WA−) and Excessive Daytime Sleepiness Negative (EDS−) requiring an odds ratio calculation, or female Witnessed Apnea Negative (WA−) and Excessive Daytime Sleepiness Negative (EDS−) requiring an odds ratio calculation;
      iii. providing a health screening service report using the categorized input information from the general coordinator to the company adapted to identify operators with high predictive values for sleep apnea; and
      iv. providing a summary of all positive predictive values using input information to the company;
   b. the sleep apnea treatment comprising:
      i. directing at least one operator to a physician to prescribe a sleep test for sleep apnea and transmitting the results of the sleep test to the general coordinator;
      ii. providing sleep apnea treatment equipment comprising a data transfer device paired with a CPAP machine comprising a compliance chip by the general coordinator to the operators indicated by the sleep apnea test data to have sleep apnea when the sleep apnea sleep test concludes;
   c. the sleep apnea treatment compliance monitoring comprising:
      i. using the data transfer device by each operator to transmit sleep apnea treatment equipment data from the sleep apnea treatment equipment to the general coordinator;
      ii. contacting each operator with sleep apnea by the general coordinator after a first predetermined period of continuous compliance monitoring to ascertain sleep apnea treatment equipment performance; and
      iii. following the first predetermined period, contacting each operator with sleep apnea periodically by the general coordinator to ascertain sleep apnea treatment equipment performance.

2. The method of claim 1, wherein after the first predetermined period further comprising the step of:
   a. returning the data transfer device by each operator with sleep apnea to the general coordinator after a second predetermined period of continuous compliance monitoring;
   b. continuing to track sleep apnea treatment equipment data for each operator with sleep apnea by the general coordinator;
   c. downloading sleep apnea treatment equipment data by each operator with sleep apnea to an encrypted removable data storage device;
   d. transferring sleep apnea treatment equipment data from the encrypted removable data storage device to a processor by the general coordinator; and
   e. compiling the sleep apnea treatment equipment data using the processor to create a compliance report.

3. The method of claim 1, wherein the input information to the general coordinator further comprises providing answers to the secure sleep apnea screening questionnaire to the general coordinator by each operator using a company device connected in encrypted communication with a network further in communication with at least one server; and wherein the at least one server communicates with an input device, an output device, and a data storage, wherein the data storage comprises encrypted computer instructions for the sleep apnea screening questionnaire, and encrypted computer instructions providing a confirmation e-mail to each operator by the server.

4. The method of claim 2, wherein the data transfer device is adapted for use with a data transfer system.

5. The method of claim 4, further comprising transmitting sleep apnea treatment equipment data from the sleep apnea treatment equipment to the general coordinator using the data transfer system.

6. The method of claim 1, wherein the sleep apnea treatment equipment data provides hours of use, data on mask leakage, and an apnea index based on throat closure during sleep apnea treatment compliance monitoring.

7. The method of claim 2, further comprising continuing to track sleep apnea treatment equipment data for each operator while complying with specified requirements established by the company after the second predetermined time of continuous compliance monitoring by the general coordinator.

8. The method of claim 7, wherein the second predetermined time of continuous compliance monitoring comprises a range between 2 weeks and 4 weeks.

9. The method of claim 2, wherein the encrypted removable data storage device comprises flash memory cards, flash drives, portable hard drives, memory cards, modems, and direct cable connections to the processor.

10. The method of claim 2, further comprising providing the compliance report for at least one of the operators with sleep apnea to the company by the general coordinator.

11. The method of claim 2, further comprising associating the compliance report and the health screening service report by the general coordinator with each operator.

12. The method of claim 1, further comprising providing delivering sleep apnea screening, sleep apnea treatment, and sleep apnea treatment compliance monitoring simultaneously on a plurality of operators and simultaneously to a plurality of companies.

13. The method of claim 1, wherein the method is complaint with the United States Health Insurance Portability and Accountability Act of 2002, 42 C.F.R. section 164.

14. The method of claim 1, further comprising providing an individualized health screening service report to the at least one operator.

15. The method of claim 1, further comprising providing the individualized health screening service report by e-mail.

16. The method of claim 1, wherein the individual personal information comprises:
 a. name of operator;
 b. an employee number for each operator;
 c. gender for each operator;
 d. social security number for each operator;
 e. an alert icon for self admitted sleep apnea;
 f. date of input of information;
 g. date of hire; or
 h. at least one company designated field.

17. The method of claim 1, further comprising compiling the results of the sleep apnea sleep test with the categorized input information to provide a summary of data of the sleep apnea sleep test administered to the operator with the categorized input information.

18. The method of claim 1, further comprising the step of generating a health screening survey report for the company comprising a member of the group comprising of:
 a. company name;
 b. gender of operator;
 c. presence or absence of sleep apnea;
 d. body mass index;
 e. presence or absence of hypertension;
 f. presence or absence of diabetes;
 g. presence absence of heart disease;
 h. neck size;
 i. presence or absence of lung disease;
 j. presence or absence of asthma;
 k. presence or absence of heart burn;
 l. an indicator for frequent urination at night; and
 m. combinations thereof.

19. The method of claim 1, further comprising flagging operators with self admitted sleep apnea for additional validation data supporting self admitted sleep apnea.

20. The method of claim 18, wherein the health screening service report comprises a look-up table for each operator by name, employee number, or social security number.

21. The method of claim 18, further comprising creating additional reports comprising:
 a. sleep test results;
 b. compliance reports; or
 c. receipts verifying delivery of equipment.

22. The method of claim 1, further comprising confirming the company has a United States Health Insurance Portability and Accountability Act of 2002 42 CFR section 164, compliant release for each operator.

23. The method of claim 1, wherein the secured sleep apnea diagnostic screening questionnaire comprises:
 a. company employee information;
 b. individual personal information; and
 c. personal health information.

24. The method of claim 1, wherein the sleep apnea screening further comprises completing a situational questionnaire comprising gender related questions.

25. The method of claim 18, wherein the health screening service report comprises:
 a. at least one rating per operator, wherein the rating comprises an member of the group consisting of:
 b. individualized numerical scores indicating a positive predictive value for the operator;
 c. a high, medium, or low positive predictive value for each operator; or combinations thereof.

* * * * *